United States Patent
Ready et al.

(10) Patent No.: US 10,166,085 B2
(45) Date of Patent: Jan. 1, 2019

(54) METHOD OF DISINFECTING PORTS IN CENTRAL VENOUS CATHETER SYSTEMS

(71) Applicants: William Judson Ready, Atlanta, GA (US); Pranav Godbole, Peachtree City, GA (US); Bharathwaj Nandagopal, Middletown, DE (US); Mary Catherine Adams, Roswell, GA (US); Timothy Gassner, Santa Ana, CA (US); You Keun Kim, Daegu (KR); Ruifu Shi, Zurich (CH)

(72) Inventors: William Judson Ready, Atlanta, GA (US); Pranav Godbole, Peachtree City, GA (US); Bharathwaj Nandagopal, Middletown, DE (US); Mary Catherine Adams, Roswell, GA (US); Timothy Gassner, Santa Ana, CA (US); You Keun Kim, Daegu (KR); Ruifu Shi, Zurich (CH)

(73) Assignee: Hub Hygiene, Atlanta, GA (US)

( * ) Notice: Subject to any disclaimer, the term of this patent is extended or adjusted under 35 U.S.C. 154(b) by 0 days.

(21) Appl. No.: 15/498,447

(22) Filed: Apr. 26, 2017

(65) Prior Publication Data
US 2017/0333156 A1    Nov. 23, 2017

Related U.S. Application Data

(60) Provisional application No. 62/327,470, filed on Apr. 26, 2016.

(51) Int. Cl.
A61B 90/70    (2016.01)
A61L 2/235    (2006.01)
A61M 25/00    (2006.01)
A61M 39/16    (2006.01)

(52) U.S. Cl.
CPC .............. *A61B 90/70* (2016.02); *A61L 2/235* (2013.01); *A61M 39/16* (2013.01); *A61L 2202/24* (2013.01); *A61M 2025/0019* (2013.01)

(58) Field of Classification Search
CPC . A61B 90/70; A61L 2/235; A61M 2025/0019
See application file for complete search history.

(56) References Cited

U.S. PATENT DOCUMENTS

| | | | |
|---|---|---|---|
| 8,065,773 | B2 | 11/2011 | Vaillancourt et al. |
| 8,069,523 | B2 | 12/2011 | Vaillancourt et al. |
| 8,336,151 | B2 | 12/2012 | Kerr et al. |

(Continued)

OTHER PUBLICATIONS

Holroyd et. al., "Universal intravenous access cleaning device fails to sterilize stopcocks," Anesth Analg. Feb. 2014; 118(2):333-43.

*Primary Examiner* — Kevin Joyner
(74) *Attorney, Agent, or Firm* — Troutman Sanders LLP; Ginger G. Turner; Ryan A. Schneider

(57) ABSTRACT

The present disclosure generally relates to systems for disinfecting Central Venous Catheter (CVC) system ports that use highly-abrasive and highly-conforming foam material in place of wipes or other sponge products, and methods for using such systems. The foam material may be an open-cell microabrasive material such as melamine foam. The foam material may contain disinfecting solutions such as isopropyl alcohol, chlorhexidine gluconate, or povidone-iodine.

4 Claims, 3 Drawing Sheets

(56) References Cited

U.S. PATENT DOCUMENTS

| | | |
|---|---|---|
| 8,336,152 B2 | 12/2012 | Vaillancourt et al. |
| 8,635,732 B2 | 1/2014 | DeDominicis et al. |
| 8,671,496 B2 | 3/2014 | Vaillancourt et al. |
| 9,186,707 B2 | 11/2015 | Vailllancourt et al. |
| 9,192,449 B2 | 11/2015 | Kerr et al. |
| 2010/0064456 A1* | 3/2010 | Ferlic ..................... A61L 2/235 15/104.94 |
| 2017/0274198 A1* | 9/2017 | DuPont ............... A61M 39/162 |

* cited by examiner

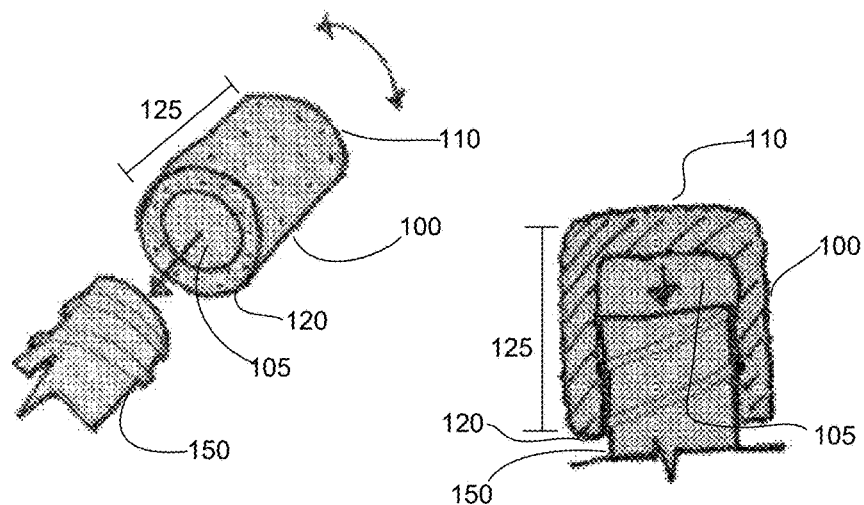
FIG. 1 A          FIG. 1B
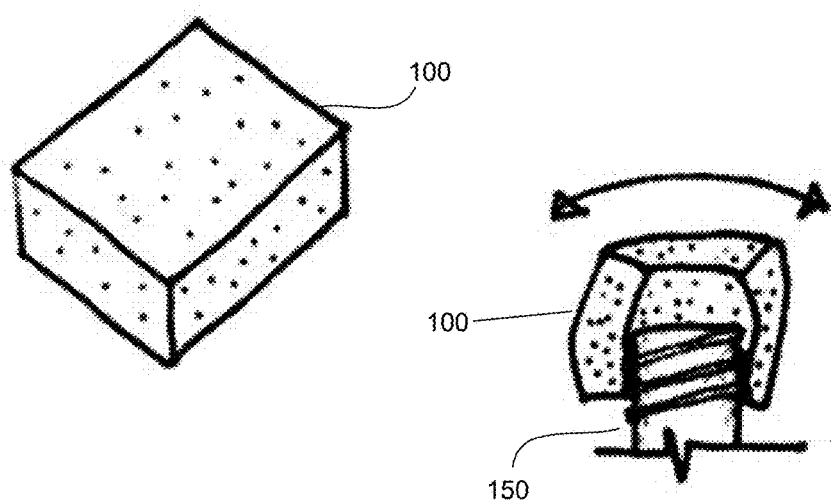
FIG. 2A          FIG. 2B

METHOD OF DISINFECTING PORTS IN CENTRAL VENOUS CATHETER SYSTEMS

CROSS-REFERENCE TO RELATED APPLICATION

This application claims the benefit under 35 U.S.C. § 119(e) of U.S. Provisional Patent Application No. 62/327,470, filed Apr. 26, 2016, the content of which is incorporated herein by reference in its entirety.

FIELD OF INVENTION

The present disclosure relates to medical device safety and, more particularly, to an apparatus and method for disinfecting connector hubs, also referred to as ports, in central venous catheter (CVC) systems (also known as central line systems).

BACKGROUND

The development of needleless intravenous (IV) administrative systems began in the 1990s to protect against needle stick injuries, which proved dangerous due to the increased spread of blood-borne diseases. The IV systems also provided a means for connecting multiple medicines to a patient without additional needles, thus aiding healthcare professionals and easing patient discomfort.

Unfortunately, these IV systems lead to an estimated 250,000 IV device-related bloodstream infections (BSIs) each year in the United States. Each case has an attributable mortality rate of between 12 and 25 percent. It is estimated that these preventable infections make up 4% of medical malpractice claims on doctors and cause hospitals to lose an estimated $9B annually because of non-reimbursed litigation costs.

In intensive care units (ICUs), bloodstream infections (BSIs) caused by bacterial contamination of the connector hubs in central venous catheter systems, or central line systems, (central line-associate bloodstream infections, CLABSI) are prevalent and yet avoidable. Although CLABSIs are listed as "Never events" by Medicare due to their preventability, in the United States, over 40,000 people are infected by CLABSIs annually, of which over 10,000 die. An average case of CLABSI costs the hospital an estimated $46,000.

A majority of CLABSIs are caused by bacteria introduced into the patient's bloodstream via contamination of the system ports. Every port on the system including injection ports into bags or bottles, injection ports on administration sets, needless connectors, and the hub of the catheter itself are a potential entry point for infection. Contamination occurs when bacteria migrate from the skin-catheter interface, along the length of the catheter, down the lumens, and finally settle on the system ports. The system ports provide a safe and nutritious environment for the bacteria to colonize, and within 3-5 days, the bacteria may form a biofilm. Biofilm organisms are far more resistant to antimicrobial agents than are organisms in suspension, and biofilms exhibit strong adherence to the surface of habitable environments. Combating this occurrence requires routine connector disinfection using not only effective antimicrobial agents, but also a mechanical force component to penetrate the biofilm and break surface adhesion.

The "Scrub the Hub" (STH) protocol issued by the Center for Disease Control (CDC) establishes an approach to clean ports to eliminate the risk of BSIs. Typically, alcohol- or chlorhexidine-soaked swabs or wipes are used to abrasively scrub the components of an IV system for a given period of time to remove viruses, bacteria, yeast, fungi, and other biofilms that can cause BSIs.

Unfortunately, research suggests that IV systems often are not scrubbed for the recommended duration or with the proper amount of friction to remove biofilms. For example, the STH protocol recommends cleaning IV ports with swabs or wipes for at least 15 seconds and some facilities recommend cleaning for 30 seconds, but current estimates reveal that most healthcare professionals clean the IV ports for approximately nine seconds.

Previous attempts to reduce the number of CLABSI incidents include a variety of approaches including addressing both behavioral and technological issues. Because every port on the system provides an entry point for infection, there are many different potential CLABSI incident triggers. Previous attempted solutions include, for example, protocol changes, modifications to the ports themselves, port caps containing disinfectant, chemical changes in the disinfecting solutions used in wipes (e.g., using chlorhexideine or povidone-iodine in place of or addition to isopropyl alcohol), port cleaners specialized for certain types of system ports, and color changing wipes. Despite these attempts, CLABSI incidents persist.

There is a need, therefore, for a user-friendly, low-cost, more efficient scrubbing product that is capable of effectively disinfecting the variety of CVC system ports.

SUMMARY

Embodiments of the disclosed technology include systems and methods for disinfecting central venous catheter (CVC) system ports. Aspects of the present disclosure provide systems and methods that optimize sanitation effectiveness, while adhering to the current STH protocol to decrease CLABSI rates. Further aspects of the present disclosure can aid in reducing the number of CLABSI incidents where non-compliance with STH protocol commonly occurs.

Some embodiments disclosed include a foam scrubber composed of an open-cell microabrasive foam, such as, for example, formaldehyde-melamine-sodium-bisulfite foam ("melamine foam"). The present disclosure also relates to methods for disinfecting a CVC system port that include, in some embodiments, scrubbing the CVC system port in a twisting motion with the foam scrubber that contains a disinfecting solution.

In some embodiments, the foam scrubber may be configured to provide audible feedback to a user when the user scrubs a CVC catheter hub with the scrubber in a twisting motion with an appropriate force to remove a biofilm that may be present on the CVC catheter hub.

In some embodiments, the foam material may have no linear dimension greater than 3 centimeters. The foam scrubber may be disposable and packaged in a liquid-impermeable pouch, and the pouch may be scored or provide some means for being easily torn open during use. The disinfecting solution may contain a 70% isopropyl alcohol solution and may further contain a chlorhexideine solution, a povidone-iodine solution, or both.

The foam scrubber material may have a block or cube shape. Alternatively, the foam scrubber may have a cylindrical shape with a hollow center and an open end such that the scrubber is configured to be put over the top of a CVC catheter hub or other system port (similar to how a cap might be placed over a hub or port) wherein the hollow center of the scrubber has the appropriate dimensions to fit over the hub or port. For example, given standard dimensions of a CVC catheter hub, a cylindrical hollow center of the scrubber having a diameter of at least 7 millimeters but not more than 8 millimeters would be capable of fitting over a CVC catheter hub.

Additional features and advantages are realized through the techniques of the present disclosure. Other embodiments and aspects of the disclosed technology are described in detail herein and are considered a part of the claimed embodiments. For a better understanding of the disclosed embodiments with the advantages and the features, refer to the description and the drawings.

BRIEF DESCRIPTION OF THE DRAWINGS

The subject matter which is regarded as the invention is particularly pointed out and distinctly claimed in the claims at the conclusion of the specification. The forgoing and other features and advantages of the disclosed embodiments are apparent from the following detailed description taken in conjunction with the accompanying drawings in which:

FIGS. 1A and 1B depict an example scrubber, according to some embodiments of the present disclosure.

FIGS. 2A and 2B depict an example scrubber, according to some embodiments of the present disclosure.

DETAILED DESCRIPTION

Figure 3A:
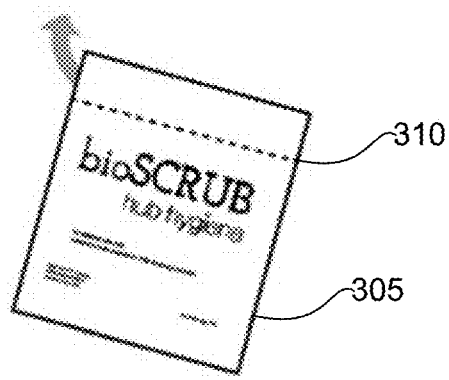
FIGS. 3A, 3B, and 3C illustrate usage of an example scrubber according to some embodiments of the present disclosure.

Although example embodiments of the present disclosure are explained in detail herein, it is to be understood that other embodiments are contemplated. Accordingly, it is not intended that the present disclosure be limited in its scope to the details of construction and arrangement of components set forth in the following description or illustrated in the drawings. The present disclosure is capable of other embodiments and of being practiced or carried out in various ways.

It must also be noted that, as used in the specification and the appended claims, the singular forms "a," "an" and "the" include plural referents unless the context clearly dictates otherwise. Ranges may be expressed herein as from "about" or "approximately" one particular value and/or to "about" or "approximately" another particular value. When such a range is expressed, other exemplary embodiments include from the one particular value and/or to the other particular value.

By "comprising" or "containing" or "including" is meant that at least the named compound, element, particle, or method step is present in the composition or article or method, but does not exclude the presence of other compounds, materials, particles, method steps, even if the other such compounds, material, particles, method steps have the same function as what is named.

In describing example embodiments, terminology will be resorted to for the sake of clarity. It is intended that each term contemplates its broadest meaning as understood by those skilled in the art and includes all technical equivalents that operate in a similar manner to accomplish a similar purpose. It is also to be understood that the mention of one or more steps of a method does not preclude the presence of additional method steps or intervening method steps between those steps expressly identified. Steps of a method may be performed in a different order than those described herein without departing from the scope of the present disclosure. Similarly, it is also to be understood that the mention of one or more components in a device or system does not preclude the presence of additional components or intervening components between those components expressly identified.

Certain embodiments of the disclosed technology provide an apparatus and method for properly cleaning medical equipment according to prescribed guidelines. In particular, certain embodiments provide an apparatus and a method for a low-cost, highly abrasive, foam scrubber for disinfecting a variety of IV system ports in a shortened period of time compared to existing methods.

Certain embodiments include a scrubber composed of formaldehyde-melamine-sodium-bisulfite foam, also known as melamine foam, that is impregnated with a disinfecting solution. As will be appreciated, melamine foam has several advantages over wipes that are typically used for cleaning CVC system ports. Melamine foam is more abrasive and thereby more effective at removing biofilms through friction, meaning that CVC system ports can be disinfected in a shorter scrubbing time compared to wipes. Melamine foam is fiberless and thereby will not leave behind fibers like a wipe typically used in this application. Melamine foam is highly conformal and therefore more effective at cleaning small crevices such as luer threads. Melamine foam has an open cell structure that allows for capillary forces to draw infectious agents up and away from the surface of a CVC system port, whereas a wipe may spread around and leave behind material. When melamine foam is applied to a system port with a twisting motion producing sufficient friction force to remove biofilms, the frictional force generates an auditory feedback, "squeak", that informs the user that biofilms are being removed. Additionally, the cost of a scrubber composed of melamine foam is comparable in price to a wipe typically used to clean CVC system ports, and in some embodiments, may be capable of cleaning the variety of CVC system ports. A scrubber composed of melamine foam is therefore a viable and more effective replacement to a wipe.

Attempts have been made to replace wipes with cleaning products or caps that use a foam material. Such products use a semi-closed hydrophilic polyurethane medical grade foam. Prior attempts to utilize foam for cleaning system ports have been unsuccessful at being a viable replacement for wipes. Such foam-based products are designed for cleaning female luers wherein the hydrophilic polyurethane foam is encased in a housing with an open end for inserting female luers. Therefore, such prior designs are not effective at cleaning all CVC system ports. For example, the prior foam-based designs are not successful in disinfecting conventional open lumen stopcock device rims compared to wipes according to, for example, Holroyd et. al., "Universal intravenous access cleaning device fails to sterilize stopcocks," Anesth Analg. 2014 February; 118(2):333-43. Additionally, prior foam-based devices are not a viable alternative to wipes because they are significantly more expensive than wipes. Melamine foam has several advantages over semi-closed hydrophilic polyurethane foam. Unlike hydrophilic polyurethane foam, melamine foam is more abrasive, more conformal, thus allowing for greater diversity in cleaning CVC system ports and components, and provides an auditory feedback during proper use.

Despite the advantages of melamine foam described above, melamine is not commonly used in medical devices.

One explanation for the continued use of wipes in cleaning medical devices is the broad applicability of wipes in cleaning applications. In addition to medical devices, wipes can be used, for example, to disinfect skin. Melamine foam, however, is not as biocompatible as wipes. So while melamine foam is a viable replacement for wipes in the application of cleaning CVC system ports, due to the abrasive nature of melamine foam, it may not be a viable solution for other applications in which wipes are used such as, for example, cleaning skin.

FIGS. 1A, 1B, 2A, and 2B illustrate various embodiments of scrubbers 100 that are composed of a highly conforming, abrasive, and porous foam material that is impregnated with a disinfecting solution, according to the present disclosure. FIGS. 1A and 1B show an example embodiment of a scrubber 100 having a cylindrical shape with a hollow center 105, a closed end 110, an open end 120, and a length 125. The scrubber 100 is designed to fit over a system port 150 such that when in use, the scrubber 100 can be configured to make simultaneous contact with the sides and top of the port 150. Currently, the size of small-bore connections in hypodermic application of medical devices and accessories, such as system port 150, is standardized under ISO 80369-7: 2016. Accordingly, the present disclosure contemplates that the diameter of the hollow center 105 and the length 125 may be designed to accommodate system ports 150 meeting the ISO standard.

In other embodiments, such as shown in FIGS. 2A and 2B, the scrubber 100 may have a simple cube or block shape. The block shape may be sized to provide an ergonomic hand grip. For example, the *Human Engineering Design Data Digest* issued by the Department of Defense Human Factors Engineering Technical Advisory Group in Washington D.C. issued April 2000 indicates a scrubber sized approximately two centimeters in height and/or length may provide an ergonomic fit to hand grip. And tests indicate that a scrubber 100 sized between two and three centimeters in height and length provides the proper ergonomics to properly clean a CVC system port.

In certain use cases, a technician or other user of embodiments of the disclosed scrubber (e.g., 100 of FIG. 1A, 1B, 2A, or 2B) may press the scrubber 100 against the system port 150 in a manner resulting in conformal contact between the scrubber 100 and the sides and the top of the port 150. Embodiments can be configured such that a user can twist the scrubber 100 around the sides of the port 150 and that the scrubber 100 can be scrubbed against the top of the port 150 during use. As will be appreciated, the form-fitting characteristics of the scrubbing device 100 can allow the entire system port 150 to be cleaned, particularly the luer threads and the septum. As will be appreciated further, the highly abrasive foam material, in conjunction with the disinfecting solution that is impregnated within the material can sanitize the system port 10 and remove any bacteria.

Figure 3B:
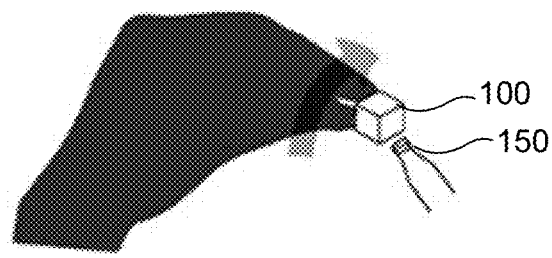
Figure 3C:
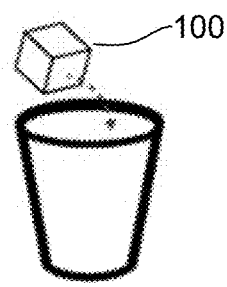

FIGS. 3A, 3B, and 3C show usage of an example scrubber (e.g., 100) according to some embodiments. As shown in FIG. 3A, in some embodiments, a scrubber 100 can be packaged within a liquid impermeable package 305. The user may open the package 305 by tearing along a scored line 310, for example. Once open, the user can extract the scrubber 100 from the package 305 and apply the scrubber 100 to a system port 150 in a twisting motion, drawing any infectious agents into the scrubber 100 as shown in FIG. 3B. Once sanitation is complete, the scrubber 100 containing the infectious agents can be discarded in a trash bin as shown in FIG. 3C. As will be appreciated, various embodiments of a scrubber 100 having a block shape as depicted in FIGS. 2A and 2B, a cylindrical shape as depicted in FIGS. 1A and 1B, or some other shape may be used in the manner shown in FIGS. 3A, 3B, and 3C.

Figure 4:
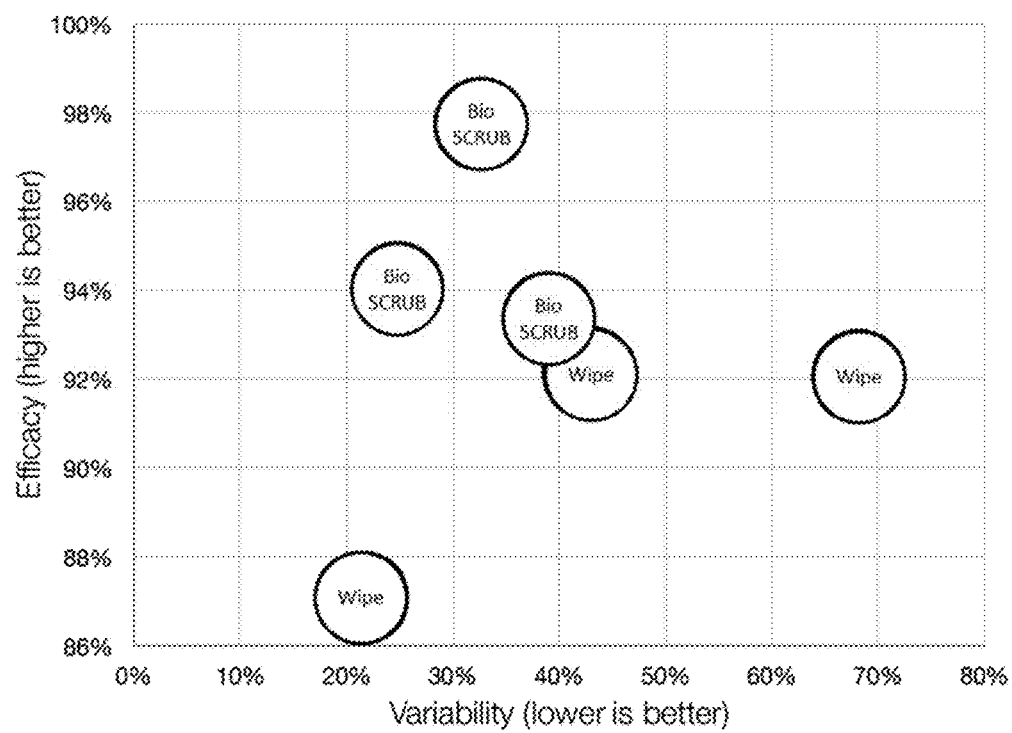
FIG. 4 illustrates data comparing the use of an example scrubber according to some embodiments of the present disclosure versus the use of a wipe.

FIG. 4 illustrates data from tests using example embodiments of a melamine foam scrubber containing a 70% isopropyl alcohol (IPA) solution, as indicated by the "BioSCRUB" data points, and data from using non-woven IPA prep pads. Initial tests of present embodiments indicate the scrubber foam material may remove at least 50% more *Escherichia coli* from a connector hub compared to a non-woven IPA prep pad used under identical STH conditions.

What is claimed:

1. A method for disinfecting a Central Venous Catheter (CVC) system port, the method comprising:
    scrubbing the CVC system port in a twisting motion with a formaldehyde-melamine-sodium-bisulfite foam material, wherein the foam material contains a disinfecting solution;
    listening for an audible feedback resulting from a friction force between the foam material and the CVC system port; and
    adjusting the friction force between the foam material and the CVC system port to produce the audible feedback.

2. The method of claim 1, wherein the audible feedback provides an indication that the friction force is capable of removing a biofilm on the CVC system port.

3. The method of claim 1, wherein the disinfecting solution contains at least one of a 70% isopropyl alcohol solution, a chlorhexidine gluconate solution, or a povidone-iodine solution.

4. The method of claim 1, wherein the CVC system port is a CVC catheter hub.

* * * * *